United States Patent [19]
Johnson

[11] 4,373,391
[45] Feb. 15, 1983

[54] RELATIVE HUMIDITY SENSITIVE MATERIAL

[75] Inventor: Peter D. Johnson, Schenectady, N.Y.

[73] Assignee: General Electric Company, Schenectady, N.Y.

[21] Appl. No.: 257,081

[22] Filed: Apr. 24, 1981

Related U.S. Application Data

[63] Continuation-in-part of Ser. No. 52,083, Jun. 26, 1979, abandoned.

[51] Int. Cl.$^3$ .......................................... H01C 13/00
[52] U.S. Cl. ...................................... 73/335; 73/336.5;
    252/187.1; 252/187.31; 252/194; 252/512;
    252/518; 252/521; 338/35; 252/963
[58] Field of Search ......................... 73/335, 336.5, 29;
    338/35; 361/256; 252/187.1, 187.31, 194, 408,
    521, 518, 512

[56] References Cited

U.S. PATENT DOCUMENTS

| | | | |
|---|---|---|---|
| 1,027,333 | 5/1912 | Herschkowitsch | 252/187.31 X |
| 2,481,728 | 9/1949 | Dember | 73/336.5 X |
| 2,535,492 | 12/1950 | Flosdolf | 252/194 |
| 2,775,511 | 12/1956 | Geffroy et al. | 422/167 |
| 3,022,667 | 2/1962 | Wexler et al. | 73/336.5 |
| 3,272,755 | 9/1966 | Shiraeff | 252/187.1 |
| 3,345,596 | 10/1967 | Delaney et al. | 324/65 P |
| 3,862,866 | 1/1975 | Timmerman et al. | 252/187.31 |
| 3,890,703 | 6/1975 | Frazee et al. | 338/35 X |
| 4,041,379 | 9/1977 | Matsuura et al. | 252/194 X |
| 4,073,741 | 2/1978 | Heintz | 252/187.31 X |

Primary Examiner—Edward R. Kazenske
Assistant Examiner—Thomas P. Noland
Attorney, Agent, or Firm—Lawrence D. Cutter; James C. Davis, Jr.; Marvin Snyder

[57] ABSTRACT

A relative humidity sensitive material comprises a mixture of at least one hygroscopic salt and an at least partially electrically conductive metal based powder. Each salt in the relative humidity sensitive material has a cationic constituent selected from the group consisting of the alkali and alkaline earth metals and an anionic constituent selected from the group consisting of a chlorate, perchlorate, and chloro aluminate. The metal based powder preferably comprises a metal or metal oxide powder or powder mixture including such constituents as Zr, $CO_3O_4$, and $MnO_2$. Additionally, the material may include a binding agent and a slurry mixture may be formed for placement of the resultant material between electrodes on a substrate so as to form a relative humidity sensor. These sensors are employed either individually or configured in a system used to either indicate or control the relative humidity.

12 Claims, 4 Drawing Figures

RELATIVE HUMIDITY SENSITIVE MATERIAL

This application is a continuation-in-part of Ser. No. 52,083 filed June 26, 1979 and now abandoned.

BACKGROUND OF THE INVENTION

This invention relates to relative humidity sensitive materials and, in particular, to materials comprising a mixture of certain salts and certain metals or metal oxides in an appropriate binder.

There is a long established need to both measure and control the relative humidity in both home and industrial environments. Whether the need is for an indication of the ambient relative humidity or for control of the relative humidity, it is first necessary to provide a transducing instrument or sensor having characteristics which depend upon the ambient relative humidity. In the past, many hygrometric instruments have depended upon dimensional variations in various materials to indicate the relative humidity. Historically significant among such devices is the well-known hair hygrometer which depends for its operation on the expansion and contraction of a fiber such as hair. These dimensional changes are then employed to move a mechanical linkage assembly which is typically connected to a mechanical dial indicator. Other hygrometric devices depend for their operation upon swelling of the material upon exposure to high level relative humidity. Again dimensional changes associated with this swelling are typically converted to appropriate mechanical movement for indicating the degree of swelling and consequently the level of relative humidity associated therewith. Many of these devices are unreliable and inaccurate. Additionally, hygrometric materials based upon dimensional changes frequently undergo long term degradation in performance following repeated cycling from low to high relative humidity and back again.

More recent relative humidity sensors are based on changes in electrical characteristics of materials in response to exposure to environments exhibiting a range of relative humidity conditions. These hygrometric materials typically exploit the variation in electrical resistance exhibited by these materials. For example, in U.S. Pat. No. 3,703,697, issued Nov. 21, 1972 to Nicholas, there is apparently described the relative humidity sensor in which an iron oxide powder ($Fe_2O_3$) is fired onto a substrate and treated with a solution of ferric chloride ($FeCl_3$). The Nicholas' relative humidity sensor appears to be based solely upon the variation of the resistance of this treated material and it further appears that it is the object of Nicholas to treat the iron oxide with ferric chloride to reduce the range of variation over which the resistance varies in accordance with variations in the ambient relative humidity. However, it is also seen that the reduction in the range over which the resistance varies through the formation of oxychlorides results in distortion of the otherwise linear graph of resistance (on logarithmic scale) versus relative humidity (on a linear scale).

For certain applications in which humidity sensors are desired in feedback control systems, the object of which is to maintain the relative humidity at a fixed or in a narrow range of temperatures, it is highly desirable to be able to produce a relative humidity sensor which is particularly responsive in the desired region of control. Conventional relative humidity sensors and materials, including those of Nicholas above, do not appear to be amenable to treatment which seek to adjust their responses to fit specific relative humidity ranges.

Other relative humidity sensors also appear to be based on the electrical properties of certain metal oxides. In particular, U.S. Pat. No. 3,345,596, issued Oct. 3, 1967 to Delaney et al. appears to disclose the use of cobalt oxide as such a material. This sensor appears to be produced by firing a substrate containing cobaltic oxide ($Co_3O_4$) deposited on a substrate to produce cobaltous oxide (CoO) having a highly crystalline surface. The resultant sensor appears to produce a variation in resistance in response to relative humidity changes over a four to five order of magnitude range. As indicated in the above-mentioned Nicholas patent, such a dynamic range of variation is undesirable in terms of the electronic circuitry which must conventionally interface with such a device to provide an indication of the relative humidity. Additionally, there is no disclosure in the patent of Delaney et al. to indicate how a hygrometric sensor may be tailored to various humidity ranges.

SUMMARY OF THE INVENTION

In accordance with a preferred embodiment of the present invention, a relative humidity sensitive material comprises a mixture of at least one hygroscopic salt and an at least partially electrically conductive metal based powder. Each said salt has a cationic constituent and an anionic constituent, as do salts generally, and, in a preferred embodiment of the present invention, the cationic constituent is selected from the group consisting of the alkali and alkaline earth metals and the anionic constituent is selected from the group consisting of chlorate, perchlorate, and chloro aluminate. The at least partially electrically conductive metal based powder preferably comprises a mixture of zirconium and cobaltic oxide ($Co_3O_4$). The mixture is conveniently bonded together with an inert binding material such as polyvinylpyrollidone or any other conventional inert hydrophilic binding material. The resulting relative humidity sensitive material is disposed between electrically conductive electrodes placed on an inert substrate to form a relative humidity sensor. A plurality of these sensors are configured in a selectable array, with the sensors in the array exhibiting overlapping response ranges.

Accordingly, it is an object of the present invention to provide a humidity sensitive material capable of readily being used to produce a relative humidity sensor having a wide or narrow response range as desired and being particularly responsive to relative humidity changes in various narrow ranges.

DETAILED DESCRIPTION OF THE INVENTION

In accordance with a preferred embodiment of the present invention, a relative humidity sensitive material comprises a mixture of at least one hygroscopic salt and an at least a partially conductive metal based powder. Each of the salts present has a cationic constituent selected from the group consisting of the alkali and alkaline earth metals and an anionic constituent selected from the group consisting of chlorate, perchlorate, and chloro aluminate. The relative humidity sensitive material of the present invention also preferably includes an inert binder such as polyvinylpyrollidone. Typical preferred salts that may be employed in the present invention include, but are not limited to, potassium perchlorate, sodium perchlorate, hydrated calcium chlorate, sodium chlorate, and hydrated barium chlorate. These salts may be employed individually or in combination.

In general, however, the salt or salt mixture comprises salts having an anionic constituent selected from the group consisting of chlorate, perchlorate, and chloro aluminate, and a cationic constituent selected from the group consisting of the alkali and alkaline earth metals. The metal based powder preferably comprises a mixture of zirconium and cobaltic oxide ($Co_3O_4$). In fact, the preferred weight ratio of Zr powder to $Co_3O_4$ powder is in the range of between 0.2 to 0.8. However, cobaltic oxide may be employed alone or with other metal powders or metal oxide powders including manganese oxide ($MnO_2$). The significant properties of the metal based powder are that it be at least partially electrically conductive and that it comprises a metal powder, a metal oxide powder or a mixture thereof.

Figure 1:
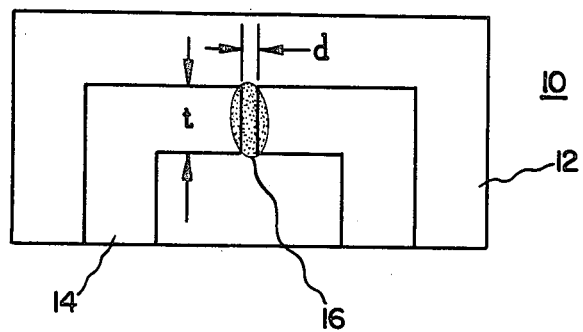
FIG. 1 is a top view of a relative humidity sensor in accordance with the present invention.

FIG. 1 illustrates a relative humidity sensor employing relative humidity sensitive material of the present invention. Electrically conductive electrodes 14 are disposed on inert substrate 12 as shown with the material 16 of the present invention affixed to the substrate 12 so as to bridge the pair of electrodes with which the material is in electrical contact. The resultant sensor 10 shown in FIG. 1 is easily fabricated. The desired salt and metal base powder is selected and mixed, as is more particularly described below, and an inert hydrophilic binding material such as polyvinylpyrollidone is added to form a slurry which is allowed to set in place. The electrodes comprise any conventional, electrically conductive material suitable for such a purpose, such as aluminum. The substrate comprises any inert material, such as glass or porous ceramic. The electrode portions between which the slurry is deposited is configured to have a width t and a separation d, as shown in FIG. 1. By way of example, and not limitation, d may be approximately 1 millimeter and t may be approximately 3 millimeters for proper operation. However, shrinkage of all dimensions by a factor of 10 is also possible without significantly impairing the operation of the sensor. Accordingly, the relative humidity sensor of the present invention is highly compatible with present-day microminiaturized solid-state devices and packaging tehcniques.

The material of the present invention not only exhibits significant changes in resistance in response to changes in the ambient relative humidity but also exhibits significant changes in the effective capacitance of a sensor such as that shown in FIG. 1. In general, the relative humidity indicated by devices of the present invention may be discerned through measuring either the resistance, the capacitance, or in general the impedance of the sensor. Even though purely resistance effects may be discerned through the use of direct currents for driving the sensor, it is highly desirable that the sensor of the present invention be operated with alternating currents to minimize problems associated with polarization and electrolysis of the sensor material. In particular, measurements described below in FIGS. 3 and 4 were acquired through the use of a 6 volt, 60 Hz drive signal. The varying impedance of the sensor of the present invention may be readily indicated through the use of a conventional bridge circuit employing a meter calibrated to read in percent relative humidity. Likewise, the sensor of the present invention may be readily incorporated in a solid-state digital device in which the analog impedance signal produced through a bridge circuit or other means is first converted to digital pulses and subsequently displayed using a light-emitting diode display or a display employing liquid crystals. The size and electrical characteristics of the present sensor are highly compatible with the use of the sensor in such solid-state electronic systems.

Figure 2:
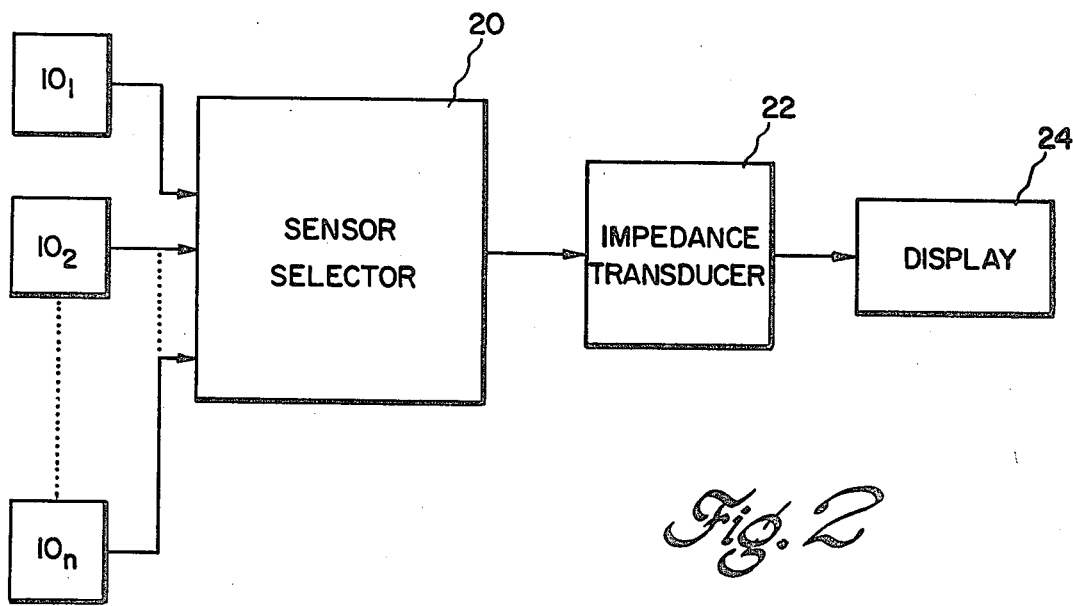
FIG. 2 is a schematic diagram illustrating the sensors of the present invention employed in a relative humidity sensing system employing the sensors of the present invention configured in a selectable array.

However, the relative humidity sensor of the present invention lends itself to other applications than merely indicating the ambient relative humidity. In particular, in certain applications it is highly desirable that the relative humidity in a particular environment be controlled as closely as possible and allowed to vary over a small range of values. Particular compositions of materials produced in accordance with the present invention particularly lend themselves to use in relative humidity sensors having a relatively narrow range of relative humidities to which they are maximally responsive. These compositions find particular application as sensors in feedback control systems designed to maintain a substantially constant relative humidity. Moreover, a plurality of sensors produced in accordance with the present invention each of which exhibit a variation in electrical properties over a substantially narrow range of relative humidities may nonetheless be configured in a relative humidity indicating system in which each sensor is designed to operate in a specific narrow range of relative humidities in which said sensor is most sensitive. In such a system, sensors are selected for operation depending upon the instantaneous level of relative humidity. To effect a wide range of permissible relative humidity readings, the sensors are designed to have overlapping ranges. Conventional relative humidity sensors do not exhibit the potential for these design considerations. Moreover, adjustments in the resistance range are made in the material of the present invention by varying the particle size and proportion of the zirconium powder used as indicated below. A schematic diagram illustrating such a system as shown in FIG. 2 which sensors $10_1$ through $10_n$ are shown connected to sensor selector 20 which operates to select one of the n sensors. The selection function can be automatic or manually overridden and is typically performed so that the center of the operating range for the sensor selected corresponds most closely with the actual ambient relative humidity. Once an individual sensor is selected, its electrical characteristics, that is its resistance, capacitance, or in general its impedance, are employed to determine the relative humidity. This function is accomplished by impedance transducer 22 which accepts as input an impedance dependent signal and produces as an output either an analog or digital signal indicative of the relative humidity. Display 24 functions to visually indicate the analog or digital relative humidity signal produced by impedance transducer 22. Alternatively, the readings from a plurality of the sensors may be combined in a weighted average to produce a single relative humidity indication.

Figure 3:
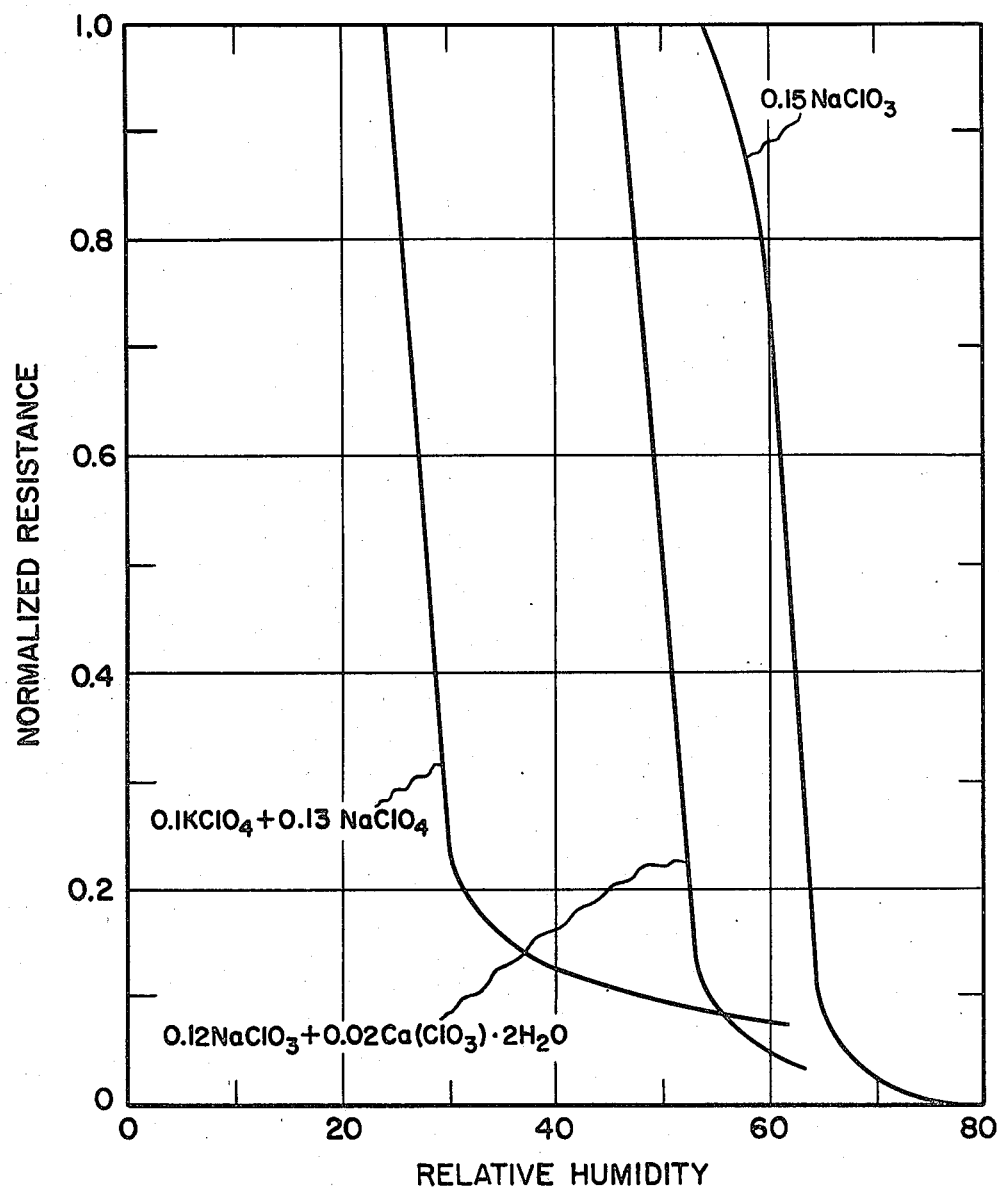
FIG. 3 is a plot of normalized resistance vs. relative humidity for certain salts and combinations of salts of the present invention.

By way of example, and not limitation, particular examples of the relative humidity sensitive material of the present invention are now described. In this description, the numbers employed indicate the weight ratio of the particular ingredient specified. In particular, a relative humidity sensitive material of the present invention may include a metal based powder with 0.4 $Co_3O_4$ and 0.45 Zr powder. The zirconium powder preferably has a particle diameter of approximately 25 microns. Adjustments of the resistance range of the sensor are made by using larger or smaller zirconium particles or varying the amounts of Zr and $Co_3O_4$. The $Co_3O_4$ employed is milled and has the consistency of lamp black. To the metal based powder there is combined a binder comprising polyvinylpyrollidone in the approximate weight ratio of between 0.005 and 0.02, but preferably approximately 0.01. To this there is also combined the hygroscopic salt or salt mixture in a weight ratio of from approximately 0.14 to approximately 0.25. The salts provide sudden change of resistivity at a critical value of relative humidity as seen in FIG. 3. Table 1 below provides a tabulation of the critical relative humidity value for several salt or salt mixtures.

TABLE I

| Active Material | $RH_{crit}$ |
| --- | --- |
| 0.1 $KClO_4$ + 0.13 $NaClO_4$ | 25 |
| 0.1 $KClO_4$ + 0.05 $NaClO_4$ | 33 |
| 0.04 $Ca(ClO_3)_2 \cdot 2H_2O$ + 0.12 $NaClO_3$ | 40 |
| 0.02 $Ca(ClO_3)_2 \cdot 2H_2O$ + 0.12 $NaClO_3$ | 50 |
| 0.5 $Ba(ClO_3)_2 \cdot H_2O$ + 0.06 $NaClO_3$ | 60 |
| 0.15 $NaClO_3$ | 70 |

A more detailed description of the variation in resistance with respect to the relative humidity of certain of the materials shown in Table I is provided in FIG. 3 for the first, fourth, and sixth salts or salt mixtures indicated in the table. The graphs shown indicate normalized resistance versus relative humidity. From these graphs, it can be appreciated that the relative humidity sensitive material illustrated are readily employable in a pluggable sensor for insertion into a relative humidity controller designed to maintain the relative humidity substantially constant in a narrow range. Selection of the desired relative humidity is accomplished by plugging an appropriate sensor into the relative humidity controller.

Figure 4:
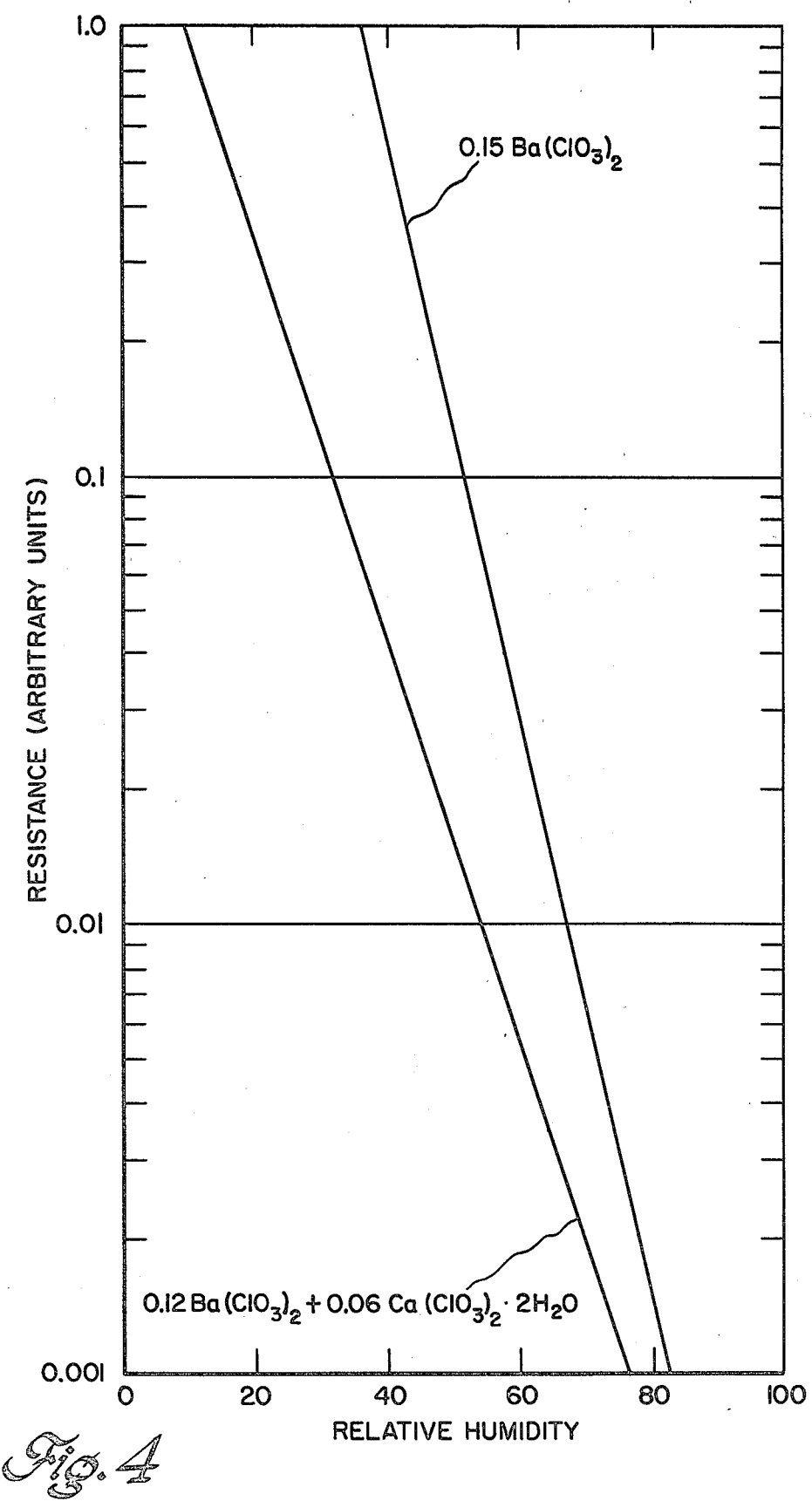
FIG. 4 is a graph of resistance vs. relative humidity for certain salts and mixtures of salts of the present invention.

For relative humidity sensitive material of the present invention exhibiting a wider range of relative humidity responses, the materials indicated in FIG. 4 may be employed. As above, in FIG. 3, only the active ingredients, that is, salts, are indicated in the figure. The same amounts of binder, $Co_3O_4$ and Zr are employed as above. As can be seen the range of relative humidity over which these ingredients exhibit a nearly linear change in resistance as measured in arbitrary units plotted on a log scale ranges from a relative humidity of approximately 10 percent to a relative humidity of approximately 80 percent. Within the range of relative humidities, the resistance varies by only three orders of magnitude. Such materials are quite appropriate for use in a relative humidity sensing system providing a digital indication of the relative humidity in a fluctuating environment. Thus, not only are these materials exhibiting a wide range of relative humidity appropriate in relative humidity indicating systems, they are also appropriate for control applications in which it is desired to selectively vary the ambient relative humidity over a wide range.

From the above, the advantages of the present invention over prior relative humidity sensing materials is easily appreciated. For example, a relative humidity sensor is easily fabricated from the relative humidity sensitive material of the present invention without the need for an expensive and costly firing process as is required in certain sensor, such as those apparently disclosed in the above-mentioned patents of Nicholas and Delaney et al. This difference in processing is further indicative of the differences in the actual materials employed in these other sensors. A significant advantage of the present invention is that the material of the invention is tailorable with respect to its resistance. In particular, increase in the proportion of $Co_3O_4$ increases the resistance at all humidities. Similarly, an increase in proportion of Zr lowers the resistance. Additionally, the materials of the present invention exhibit superior reversibility properties in that there is substantially no degradation in the device characteristics following repeated cycling between relative humidities of 15 percent and 90 percent. Relative humidity sensors employing materials of the present invention are easily fabricated on glass or ceramic substrates and are configurable in packages whose dimenions are commensurate with present-day integrated circuit techniques and a microminiature device is easily fabricated. Furthermore, it is seen that certain of the materials of the present invention which exhibit a variation in resistance over a relatively narrow range of relative humidities are particularly applicable in control circuit applications in which it is desired to maintain a substantially constant relative humidity. Also, the resistance of the material of the present invention is also controllable through size selection of zirconium powder particles.

While this invention has been described with reference to particular embodiments and examples, other modifications and variations will occur to those skilled in the art in view of the above teachings. Accordingly, it should be understood that within the scope of the appended claims, the invention may be practiced otherwise than is specifically described.

I claim:

1. A relative humidity sensitive material comprising: a mixture of at least one hygroscopic salt; an at least partially electrically conductive metal based powder comprising a mixture of materials selected from the group consisting of $Co_3O_4$, Zr, and $MnO_2$; each said salt having a cationic constituent selected from the group consisting of the alkali and alkaline earth metals and an anionic constituent selected from the group consisting of chlorate, perchlorate, and chloro aluminate; and an inert binder.

2. The relative humidity sensitive material of claim 1 in which said inert binder comprises polyvinylpyrollidone.

3. The relative humidity sensitive material of claim 1 in which said salt, metal based powder, and binder are present in the approximate weight ratio of $X:0.85:0.01$, respectively, where $0.05 \leq X \leq 0.25$.

4. The relative humidity sensitive material of claim 1 in which said at least partially electrically conductive metal based powder comprises a mixture of Zr powder and $Co_3O_4$ powder.

5. The relative humidity sensitive material of claim 4 in which the weight ratio of Zr powder to $Co_3O_4$ powder is between approximately 0.2 and 0.8.

6. The relative humidity sensitive material of claim 4 in which the particles of Zr powder have a diameter of approximately 25 microns.

7. The relative humidity sensitive material of claim 5 in which the Zr powder and the $Co_3O_4$ powder are approximately present in the weight ratio of 0.45:0.40 with respect to each other.

8. The relative humidity sensitive material of claim 1 in which said at least one salt is selected from the group consisting of $KClO_4$ and $NaClO_4$ in the approximate weight ratio of 0.1 to 0.13, respectively;

$KClO_4$ and $NaClO_4$ in the approximate weight ratio of 0.1 to 0.05, respectively;

$Ca(ClO_3)_2.2H_2O$ and $NaClO_3$ in the approximate weight ratio of 0.04 to 0.12, respectively;

$Ca(ClO_3)_2.2H_2O$ and $NaClO_3$ in the approximate weight ratio of 0.02 to 0.12, respectively;

$Ba(ClO_3)_2.H_2O$ and $NaClO_3$ in the approximate weight ratio of 0.15 to 0.06; respectively, and $NaClO_3$ in the approximate weight ratio of 0.15, each of the weight ratios being given with respect to said metal based powder which is present in the approximate weight ratio of 0.85 with respect to the above ratios.

9. The relative humidity sensitive material of claim 8 wherein the inert binder is hydrophilic and present in the weight ratio of between approximately 0.005 and approximately 0.02.

10. A relative humidity sensor exhibiting changes in impedance in response to changes in relative humidity, said sensor comprising an inert substrate with a pair of spaced apart electrodes disposed thereon with the relative humidity sensitive material of claim 1 affixed to said substrate between said electrodes and in electrical contact with said electrodes.

11. The relative humidity sensor of claim 10 in which said substrate comprises material selected from the group consisting of glass and porous ceramic.

12. A relative humidity sensing system comprising:
a plurality of sensors of claim 10, each of said sensors being particularly responsive to changes in relative humidity in a specific relative humidity range; and
means to select at least one of said sensors, said selection depending on ambient relative humidity conditions;
means to convert the impedance of said at least one selected sensor so as to indicate said ambient relative humidity.

* * * * *